US010442830B2

(12) United States Patent
Gozlan et al.

(10) Patent No.: US 10,442,830 B2
(45) Date of Patent: Oct. 15, 2019

(54) SYNTHESIS OF MONOETHERS OF SUGAR COMPRISING A LONG ALKYL CHAIN AND USES THEREOF AS A SURFACTANT

(71) Applicants: TEREOS STARCH & SWEETENERS BELGIUM, Aalst (BE); UNIVERSITÉ CLAUDE BERNARD LYON 1, Villeurbanne (FR); CENTRE NATIONAL DE LA RECHERCHE SCIENTIFIQUE, Paris (FR)

(72) Inventors: Charlotte Gozlan, Villeurbanne (FR); Marie-christine Duclos, Villeurbanne (FR); Nicolas Duguet, Villeurbanne (FR); Marc Lemaire, Villeurbanne (FR); Andreas Redl, Aalst (BE)

(73) Assignees: TEREOS STARCH & SWEETENERS BELGIUM, Aalst (BE); UNIVERSITÉ CLAUDE BERNARD LYON 1, Villeurbanne (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 166 days.

(21) Appl. No.: 15/533,361

(22) PCT Filed: Dec. 3, 2015

(86) PCT No.: PCT/IB2015/059328
§ 371 (c)(1),
(2) Date: Jun. 5, 2017

(87) PCT Pub. No.: WO2016/088076
PCT Pub. Date: Jun. 9, 2016

(65) Prior Publication Data
US 2018/0265533 A1 Sep. 20, 2018

(30) Foreign Application Priority Data
Dec. 3, 2014 (FR) .................................... 14 02755

(51) Int. Cl.
| C07H 15/04 | (2006.01) |
| C07C 43/14 | (2006.01) |
| C07C 43/15 | (2006.01) |
| C07C 43/10 | (2006.01) |
| C07C 43/04 | (2006.01) |
| C07H 1/00 | (2006.01) |
| C07D 307/20 | (2006.01) |
| C11D 1/66 | (2006.01) |
| C07H 3/02 | (2006.01) |
| B01F 17/00 | (2006.01) |
| C07H 1/06 | (2006.01) |

(52) U.S. Cl.
CPC ............. *C07H 15/04* (2013.01); *C07C 43/04* (2013.01); *C07C 43/10* (2013.01); *C07C 43/14* (2013.01); *C07C 43/15* (2013.01); *C07D 307/20* (2013.01); *C07H 1/00* (2013.01); *C07H 3/02* (2013.01); *C11D 1/662* (2013.01); *B01F 17/0021* (2013.01); *C07H 1/06* (2013.01); *Y02P 20/582* (2015.11)

(58) Field of Classification Search
CPC ..................................................... C07H 15/04
See application file for complete search history.

(56) References Cited

U.S. PATENT DOCUMENTS

| 5,429,820 A | * | 7/1995 | Kamitani | ............. | A61K 8/0295 |
| | | | | | 424/401 |
| 5,962,399 A | * | 10/1999 | Wulff | .................... | A61K 8/604 |
| | | | | | 510/276 |

FOREIGN PATENT DOCUMENTS

| GB | 0 019 888 A1 | 12/1980 |
| WO | WO 2012/148530 A1 | 11/2012 |

OTHER PUBLICATIONS

Fanton et al., "Long chain acetals derived from sucrose as a new class of surfactants", Carbohydrate Research, Feb. 20, 1997, 298:1-2:85-92.
International Search Report dated Feb. 5, 2016.

* cited by examiner

*Primary Examiner* — Eric Olson
(74) *Attorney, Agent, or Firm* — Symbus Law Group, LLC; Clifford D. Hyra

(57) ABSTRACT

A process for obtaining a mixture of C4-C8 and C9-C18 alkyl monoether of saccharide, comprising: a) a first step of acetalization or trans-acetalization of a saccharide or of a mixture of saccharides with a C4-C8 aliphatic aldehyde or the acetal thereof, b) a second consecutive or simultaneous step of acetalization or trans-acetalization of the product obtained in a) of the saccharide or mixture of saccharides with a C9-C18 aliphatic aldehyde or the acetal thereof, c) a step of catalytic hydrogenolysis of the saccharide acetals obtained, and d) a step of recovery of a mixture of C4-C8 and C9-C18 alkyl saccharide monoethers. The invention further relates to a mixture of C4-C8 and C9-C18 alkyl saccharide monoethers and the use thereof as a surfactant.

20 Claims, 1 Drawing Sheet

SYNTHESIS OF MONOETHERS OF SUGAR COMPRISING A LONG ALKYL CHAIN AND USES THEREOF AS A SURFACTANT

This application is a national stage entry of international application PCT/IB2015/059328 under 37 C.F.R. § 371, and claims the benefit of French patent application No. 14/02755, filed Dec. 3, 2014, which is hereby incorporated by reference in its entirety.

The present invention relates to a process for obtaining a mixture of C4-C8 and C9-C18 alkyl saccharide monoethers of a saccharide derivative or of mixtures thereof. The invention further relates to a mixture of C4-C8 and C9-C18 alkyl monoethers of saccharide, of a saccharide derivative or of mixtures thereof, obtainable by said method and use thereof as a surfactant.

BACKGROUND OF THE INVENTION

During last century, society became increasingly aware of and sensitized to environmental questions, and more particularly to the ecological effects of the use of chemicals in industry. This has led to an increase in the use of biodegradable products such as nontoxic biodegradable surfactants, for example. Surfactants based on sugars obtained from renewable resources represent a good solution to this need since they possess good surface-active properties. Their use as emulsifiers in the food industry and in polymerization reactions has been documented, for instance in detergents, cosmetics and surface cleaning products. Two broad categories of surfactants based on carbohydrates are now being marketed: carbohydrate-based fatty acid esters, and alkyl (poly)glycosides. The carbohydrate-based fatty acid esters are only stable over a limited range of pH, as they are hydrolyzed in acid or alkaline conditions. In contrast, the alkyl (poly)glycosides are very stable in alkaline conditions, but they are sensitive in an acid environment. The alkyl polyglycosides (APGs) are the best known in this category.

In the category of carbohydrate-based fatty acid esters, the esters of fatty acids and of sorbitol (SFAEs), of sorbitan (1,4-anhydrosorbitol), of isosorbide (1,4-3,6-dianhydrosorbitol) or of sucrose are among the nonionic surfactants that are the most readily available commercially. However, surfactants having an ester function are not stable in acid and basic conditions. To rectify this problem, the inventors proposed replacing the ester bond with an ether functionality to improve the stability of these species. However, preparation of derivatives of ethers based on carbohydrates generally requires the use of expensive and/or toxic solvents (dimethylsulfoxide, dimethylformamide, dimethylacetamide), high temperatures or steps of protection/deprotection, the use of nonrecyclable reagents, of strong bases (such as sodium or potassium hydroxide or sodium hydride), or the use of reducing agents that produce waste products or need to be hydrolyzed at the end of the reaction (such as sodium, aluminum or boron hydrides; hydrosilanes and hydrosiloxanes).

In this context, the inventors recently reported, in French patent application No. 14/01346, an efficient method of synthesis of sugar ethers by hydrogenolysis of the corresponding sugar acetals. In fact, the inventors have developed a process for synthesis of sugar ethers, with or without solvent, by a first step of acetalization or trans-acetalization using a catalyst and a second step of reduction of the sugar acetals by hydrogenolysis to obtain a mixture of regioisomers of sugar ethers. These two steps were optimized without purification of the acetal intermediates in order to reduce the overall cost of the process.

In order to obtain, at good yield, a composition having high and stable surface-active properties notably by employing a process that satisfies the industrial, economic and environmental constraints, the inventors suggested that this process could be employed for obtaining a composition of long-chain sugar ethers.

However, the inventors found that this process is not suitable for a step of acetalization using a long-chain alkyl aldehyde. In fact, when long-chain alkyl reagents are used, low yields are obtained.

There is therefore a need for a process that is economical and environmentally friendly for producing an environmentally friendly composition that has high surface-active properties that are stable over time and in the face of variations of pH.

After much experimentation, the inventors succeeded in finding a solution to the aforementioned problems. Thus, the inventors developed, for the first time, a novel route for the synthesis of long-chain alkyl saccharide monoethers having characteristics of surfactants. In fact, the inventors showed that a better yield in the synthesis of long-chain alkyl saccharide acetals can be obtained using a short-chain alkyl aldehyde as co-reactant. The inventors have developed an efficient process for the synthesis of long-chain alkyl saccharide monoethers having characteristics of surfactants using a reducing agent that does not produce any waste products (such as hydrogen) at the end of the reaction compared to other methods of ether synthesis using hydrides as the reducing agent. The process for synthesis of long-chain alkyl saccharide monoethers as proposed by the inventors can be carried out using only biosourced reactants, which are or can be synthesized from renewable raw materials (such as fatty aldehydes, which may be prepared from fatty acids, or saccharides or polyols that are obtainable from starch). The inventors have also developed a process for synthesis of long-chain alkyl saccharide monoethers comprising a reaction sequence involving two acetalization reactions and one hydrogenolysis reaction, without the need for a step of purification of the crude mixture of sugar acetals. Finally, the inventors have developed an economical, efficient and environmentally friendly means for synthesizing compositions of alkyl saccharide monoethers comprising long chains or short chains, these compositions of saccharide ethers displaying improved properties of surface tension and surface-active properties similar to those of long alkyl chain surfactants alone. The inventors have demonstrated a synergistic effect between the surfactants with short and long alkyl chains providing both a decrease in the surface tension of water and an increase in solubility of the long alkyl chain surfactant in aqueous solution.

EP 0 019 999 A1 describes the preparation of long-chain alkyl saccharide acetals, in particular of sorbitol partially substituted with acetate groups from $C_7$-$C_{30}$ aldehydes preferably comprising a 70:30 mixture of $C_{12}$/$C_{14}$ alkyl chains and of acetic acid as the reaction mixture.

Fanton E. et al.: "Long-chain acetals derived from sucrose as a new class of surfactants", Carbohydrate Research, Pergamon, GB, Vol. 298, No. 1-2, 20 Feb. 1997, pages 85-92, describes the preparation of $C_6$-$C_{18}$ higher alkyl acetals of acetylated sucrose starting from the corresponding aldehydes.

WO 2012/148530 describes compositions of monoalkyl ethers of polyols and more particularly of mono-anhydrohexitol having a $C_4$-$C_{18}$ alkyl ether radical.

DESCRIPTION OF THE INVENTION

Process for Obtaining a Mixture of Saccharide Alkyl Monoethers or a Composition Comprising a C9-C18 Saccharide Alkyl Monoether The invention relates to a process for obtaining a mixture of C4-C8 alkyl monoether of saccharide and/or of saccharide derivative and of C9-C18 alkyl monoether of saccharide and/or of saccharide derivative, said saccharide derivative being a glycosylated and/or hydrogenated and/or dehydrated saccharide, said process comprising:

a) a first step of acetalization or trans-acetalization of a saccharide, of a saccharide derivative or of mixtures thereof with a C4-C8 aliphatic aldehyde or the acetal thereof, b) a second consecutive or simultaneous step of acetalization or trans-acetalization of the product obtained in a), of the saccharide, saccharide derivative or mixtures thereof with a C9-C18 aliphatic aldehyde or the acetal thereof, c) a step of catalytic hydrogenolysis of the acetals of saccharide and/or of saccharide derivative obtained in b), and d) a step of recovery of a mixture of C4-C8 alkyl monoether of saccharide and/or of saccharide derivative and of C9-C18 alkyl monoether of saccharide and/or of saccharide derivative.

The invention also relates to a process for obtaining a composition comprising a C9-C18 alkyl monoether of saccharide and/or of saccharide derivative, said saccharide derivative being a glycosylated and/or hydrogenated and/or dehydrated saccharide, said process comprising:

a) a first step of acetalization or trans-acetalization of a saccharide, of a saccharide derivative or of mixtures thereof with a C4-C8 aliphatic aldehyde or the acetal thereof, b) a second step of acetalization or trans-acetalization of the product obtained in a), of the saccharide, saccharide derivative or mixtures thereof with a C9-C18 aliphatic aldehyde or the acetal thereof, wherein said step b) may be consecutive or simultaneous with step a)

c) a step of catalytic hydrogenolysis of the acetals of saccharide and/or of saccharide derivative obtained in b), and d) a step of recovery of a composition comprising a C9-C18 alkyl monoether of saccharide and/or of saccharide derivative.

"Acetalization" means the reaction by which an alcohol group and a carbonyl form an acetal group. This reaction is widely described in the prior art and is familiar to a person skilled in the art. "Trans-acetalization" means the reaction by which a transfer of acetal groups is performed between a carbonylated compound and another. This reaction is also familiar to a person skilled in the art.

As used here, the term "saccharide" refers to any simple carbohydrate, including the monosaccharides or substituted and unsubstituted oligosaccharides. As a general rule, possible examples of saccharides are monosaccharides, disaccharides or trisaccharides. Possible examples of a mixture of saccharides are a mixture of monosaccharides and disaccharides, or a mixture of monosaccharides and trisaccharides or of disaccharides and trisaccharides.

As used here, the term "monosaccharide" refers to polyhydroxyaldehyde (aldose) or polyhydroxyketone (ketose) and derivatives or analogs thereof. According to the invention, said monosaccharide may comprise from 4 to 7 carbon atoms. Examples of suitable monosaccharides comprise ribose, xylose, arabinose, glucose, galactose, mannose, telose, gulose, allose, altrose, idose, lyxose, ribulose, sorbose, fructose, and mixtures thereof.

Preferably, said monosaccharide unit has 6 carbon atoms, also denoted by the name "hexose". The term "hexose" refers both to aldohexoses, ketohexoses, and to derivatives and analogs thereof.

Preferably, said hexose is selected from the group consisting of glucose, mannose, galactose, allose, altrose, gulose, idose and talose.

According to one embodiment, prior to steps a) and b) of acetalization or trans-acetalization, the saccharide is glycosylated, hydrogenated and/or dehydrated to obtain an alkyl glycoside, a sugar alcohol or an anhydrosaccharide.

According to one embodiment, step a) of the process according to the invention may be preceded by a step of hydrogenation of said saccharide or may be carried out starting from a hydrogenated saccharide derivative, also called a sugar alcohol. As used here, the term "sugar alcohol", also known by the name "polyol", refers to a hydrogenated form of saccharide, such as the mono-, di- or trisaccharides, whose carbonyl group (aldehyde or ketone) has been reduced to a primary or secondary hydroxyl. Said sugar alcohol may, for example, be selected from the group consisting of erythritol, threitol, arabitol, xylitol, ribitol, mannitol, sorbitol, galactitol, iditol, volemitol, isomalt, maltitol, lactitol, maltotriitol, maltotetraitol and polyglycitol. Preferably, the sugar alcohol is sorbitol, xylitol or mannitol.

Typically, said sugar alcohol is a pentitol selected from the group consisting of xylitol, arabitol and ribitol, or a hexitol selected from a group consisting of mannitol, sorbitol, galactitol, fucitol, iditol and inositol.

Typically, step a) of the process according to the invention may be preceded by a step of hydrogenation and then of dehydration of said saccharide or may be carried out starting from a hydrogenated and then dehydrated saccharide derivative, also called an anhydrosaccharide.

An "anhydrosaccharide" is to be understood as being a saccharide obtained by dehydration, by elimination of one or more water molecules from a corresponding hydrogenated mono-, di-, tri- or oligosaccharide. A possible example of a suitable anhydrosaccharide is a monoanhydrosaccharide such as a hexitan selected from the group consisting of 1,4-anhydro-D-sorbitol (1,4-arlitan or sorbitan); 1,5-anhydro-D-sorbitol (polygalitol); 3,6-anhydro-D-sorbitol (3,6-sorbitan); 1,4 (3,6)-anhydro-D-mannitol (mannitan); 1,5-anhydro-D-mannitol (styracitol); 3,6-anhydro-D-galactitol; 1,5-anhydro-D-galactitol; 1,5-anhydro-D-talitol and 2,5-anhydro-L-iditol.

The preferred hexitan is derived from the dehydration of sorbitol to form, for example, 1,4-sorbitan, 3,6-sorbitan or 2,5-sorbitan.

According to one embodiment, the process according to the invention comprises a step of dehydration following a step of hydrogenation of a saccharide or starting from a saccharide derivative such as a sugar alcohol. Typically, a dehydration step of this kind is carried out before said step a) of first acetalization or trans-acetalization in order to obtain an anhydrosaccharide. When it is carried out on a saccharide derivative, such as a sugar alcohol, the saccharide derivative, preferably in powder form, is melted before the dehydration step. The dehydration step may be carried out with a catalyst, for example with an acid catalyst.

According to the invention, the dehydration step is carried out under a hydrogen atmosphere at a pressure preferably of about 20 to 50 bar.

Advantageously, the dehydration step is carried out at a temperature between 120 and 170° C., preferably between 130 and 140° C.

Typically, the saccharide is purified after the dehydration step, for example by crystallization, recrystallization or chromatography.

Advantageously, the saccharide derivative is a glycosylated saccharide. It may be sourced commercially or may be obtained by glycosylation of a saccharide before said step a) of first acetalization or trans-acetalization to obtain an alkyl glycoside.

As used here, the term "alkyl glycoside" refers to any saccharide, notably a monosaccharide, a disaccharide or a trisaccharide joined by a bond to an alkyl group, as described in the prior art. Typically, the saccharide may be bound to the alkyl group by an oxygen atom (an O-glycoside), a nitrogen atom (a glycosylamine), a sulfur atom (a thioglycoside), or a carbon atom (a C-glycoside). The alkyl group may have a varied chain length, and preferably the alkyl group is a C1-C4 alkyl group. An even more preferred alkyl group is a methyl or an ethyl. Alkyl glycosides may for example be selected from a group consisting of methyl glucoside, ethyl glucoside, propyl glucoside, butyl glucoside, methyl xyloside, ethyl xyloside, propyl xyloside, butyl xyloside, methyl mannoside, ethyl mannoside, propyl mannoside, butyl mannoside, methyl galactoside, ethyl galactoside, propyl galactoside and butyl galactoside.

"Mixtures thereof" means a mixture of several saccharides, a mixture of several derivatives of saccharides or a mixture of one or more saccharides with one or more derivatives of saccharides.

According to the invention, the first and/or second step of acetalization or trans-acetalization comprises:

i) optionally, a step of preheating of said saccharide or of said mixture of saccharides, preferably at a temperature between 70 and 130° C., typically between 90 and 110° C., ii) a step of addition of the aliphatic aldehyde or of a derivative of aliphatic aldehyde to said saccharide or to said mixture of saccharides, and iii) a step of addition of a catalyst, preferably an acid catalyst.

Step i) is particularly advantageous in that it may be carried out in the absence of solvent.

Preferably, the acid catalyst used in the first and/or second step of acetalization or trans-acetalization and in the dehydration step if applicable may be a homogeneous or heterogeneous acid catalyst. The term "homogeneous", as used in the expression "homogeneous acid catalyst", refers to a catalyst that is in the same phase (solid, liquid or gas) or in the same state of aggregation as the reactant. Conversely, the term "heterogeneous", as used in the expression "heterogeneous acid catalyst", refers to a catalyst that is in a different phase (solid, liquid or gas) than the reactants.

Said acid catalyst used in the first and/or second step of acetalization or trans-acetalization and in the dehydration step if applicable may be selected independently from the solid or liquid, organic or inorganic acids, the solid acids being preferred. In particular, the preferred acid catalyst is selected from para-toluenesulfonic acid, methanesulfonic acid, camphosulfonic acid (CSA) and sulfonic resins.

Typically, the first and/or second step of acetalization or trans-acetalization is carried out at temperatures between 70 and 130° C., typically between 70 and 90° C. The temperature of the reaction mixtures may vary depending on the reactants and solvents used. The reaction time is determined by the degree of conversion attained.

According to one embodiment, the first and/or second acetalization or trans-acetalization may be carried out independently with an aliphatic aldehyde or the acetal thereof, typically a linear or branched aliphatic aldehyde or the acetal thereof. The first step a) of acetalization or trans-acetalization may be carried out typically with an aliphatic aldehyde or the acetal thereof having 4, 5, 6, 7 or 8 carbon atoms, for example selected from butanal, pentanal, hexanal, heptanal, octanal and the acetal thereof. Preferably, the C4-C8 aliphatic aldehyde is a C5 aliphatic aldehyde or the acetal thereof, for example a pentanal or the acetal thereof. The second step b) of acetalization or trans-acetalization may typically be carried out with an aliphatic aldehyde or the acetal thereof having 9, 10, 11, 12, 13, 14, 15, 16, 17 or 18 carbon atoms, for example selected from nonanal, decanal, undecanal, dodecanal, tridecanal, tetradecanal, pentadecanal, hexadecanal, heptadecanal, octodecanal and the acetal. Preferably, the C9-C18 aliphatic aldehyde or the acetal thereof is a C12 aliphatic aldehyde or the acetal thereof, for example a dodecanal or the acetal thereof.

The expression "the acetal of the latter" or "acetal(s) thereof", as used for example in the expression "C4-C8 aliphatic aldehyde or the acetal thereof" or "C9-C18 aliphatic aldehyde or the acetal of the latter" covers the dialkyl acetal of the corresponding C4-C8 or C9-C18 aliphatic aldehyde. More particularly, the dimethyl or diethyl acetals of C4-C8 or C9-C18 aliphatic aldehyde are preferred.

According to one embodiment, the first step a) and/or the second step b) of acetalization or trans-acetalization may be carried out independently of one another with or without solvent. When the reaction is carried out in the presence of a solvent, the solvent is preferably a polar solvent.

Typically, the solvent may be selected from dimethylformamide (DMF), dimethylsulfoxide (DMSO), dimethylacetamide (DMA), acetonitrile ($CH_3CN$), tetrahydrofuran (THF), 2-methyltetrahydrofuran (2Me-THF), cyclopentyl methyl ether (CPME), methanol (MeOH), ethanol (EtOH), propanol (ProH), isopropanol (iProH), butanol (BuOH), dibutyl ether (DBE), methyl tert-butyl ether (MTBE) and trimethoxypropane (TMP).

Extensive experimentation led to a selection of conditions in which optimum degrees of conversion and yields are observed in the steps of acetalization or trans-acetalization. The best results were obtained when the molar ratio [(C4-C8 or C9-C18 aliphatic aldehyde or acetal thereof):(saccharide, saccharide derivative or mixtures thereof)] is between 5:1 and 1:5, preferably between 4:1 and 1:4, and advantageously between 3:1 and 1:3. The expression "molar ratio (C4-C8 or C9-C18 aliphatic aldehyde or acetal thereof):(saccharide, saccharide derivative or mixtures thereof)" denotes the molar ratio of the C4-C8 aliphatic aldehyde:(saccharide, saccharide derivative or mixtures thereof) or the molar ratio of the C9-C18 aliphatic aldehyde:(saccharide, saccharide derivative or mixtures thereof), but also the molar ratio of the C4-C8 aliphatic acetal:(saccharide, saccharide derivative or mixtures thereof) or the molar ratio of the C9-C18 aliphatic acetal:(saccharide, saccharide derivative or mixtures thereof).

The inventors have shown more particularly that in an acetalization reaction, the molar ratio of C4-C8 or C9-C18 aliphatic aldehyde:(saccharide, saccharide derivative or mixtures thereof) between 1:1 and 1:5, preferably between 1:1 and 1:4, and preferably between 1:3 and 1:2 improves the yields and provides optimum degrees of conversion.

The inventors have shown, moreover, that in the reactions of trans-acetalization, a molar ratio of C4-C8 or C9-C18 aliphatic acetal: (saccharide, saccharide derivative or mixtures thereof) between 1:1 and 5:1, preferably between 5:4 and 4:1, preferably between 3:1 and 4:3, more preferably between 3:2 and 2:5 improves the yields and provides optimum degrees of conversion. The catalysts used are the same as in the acetalization reaction.

According to one embodiment, the process of the invention further comprises at least one step of neutralization and/or filtration and/or purification after any one of the steps of dehydration if applicable, of the first step a) and/or of the second step b) of acetalization or trans-acetalization.

When a purification step is provided, said purification step may be for example crystallization, recrystallization or chromatography. Preferably, chromatography is performed using a nonaqueous polar solvent. In general, when a step of filtration and/or of purification is provided before the hydrogenolysis step, the nonaqueous polar solvent may be identical to that used in the hydrogenolysis step.

Advantageously, the hydrogenolysis step is carried out at a temperature between 80° C. and 140° C., and/or at a hydrogen pressure between 15 and 50 bar, preferably between 20 and 40 bar.

The hydrogenolysis step is carried out advantageously in a polar aprotic solvent, preferably a nonaqueous solvent. In fact, the aprotic solvents offer better conversion. Examples of aprotic solvents are, among others, non-exhaustively, the alkanes, 1,2,3-trimethoxypropane (TMP), methyl tert-butyl ether (MTBE), tetrahydrofuran (THF), 2-methyl tetrahydrofuran (2Me-THF), dibutyl ether (DBE) and cyclopentylmethyl ether (CPME). Preferably, the aprotic solvent is CPME. The alkanes are advantageous as they allow better dissolution of hydrogen in the medium. However, conversion is lower than with other aprotic solvents such as CPME. In general, among the alkanes, dodecane and heptane are preferred.

The hydrogenolysis step is preferably carried out in a polar aprotic solvent at a temperature between 80° C. and 140° C. and/or at a hydrogen pressure between 15 and 50 bar, in the presence of a suitable catalyst for hydrogenolysis reactions.

Preferably, the hydrogenolysis step is carried out in a nonaqueous polar solvent at a temperature between 100° C. and 130° C. and/or at a pressure between 25 and 35 bar.

Generally, hydrogenolysis is carried out in the presence of a suitable catalyst such as a catalyst based on precious metals or base metals. More particularly, the base metals may be ferrous or nonferrous metals. Typically, hydrogenolysis is carried out in the presence of a catalyst based on ferrous metals.

As a guide, a metal catalyst belonging to the ferrous metals group may be nickel, cobalt or iron.

Preferably, hydrogenolysis is carried out using a catalyst based on precious metals such as palladium, rhodium, ruthenium, platinum or iridium.

As a general rule, the catalyst used in hydrogenolysis may be fixed on a support such as carbon, alumina, zirconia or silica or any mixture thereof. Such a support is for example a bead. Thus, a palladium catalyst fixed on carbon beads (Pd/C) may be used advantageously. These catalysts may be doped by adding precious metals or base metals. They are called dopants. Typically, the dopant represents 1 to 10 wt % of the catalyst.

Mixture of Alkyl Saccharide Monoethers

The invention also relates to a composition comprising a mixture of positional isomers of C4-C8 alkyl monoether of saccharide and/or of saccharide derivative and positional isomers of C9-C18 alkyl monoether of saccharide and/or of saccharide derivative, notably obtainable by the process of the invention, in which the saccharide derivative is a glycosylated and/or hydrogenated and/or dehydrated saccharide, and the saccharide is a hexose. Preferably, the positional isomers of C4-C8 alkyl monoether of saccharide or of saccharide derivative and the positional isomers of C9-C18 alkyl monoether of saccharide or of saccharide derivative have alkyl groups in at least two of the positions selected from 2-O, 3-O, 4-O, 5-O and 6-O.

Typically, when the saccharide derivative is an alkyl glycoside the positional isomers are at least two of 2,O-alkyl monoether, 3,O-alkyl monoether—4,O-alkyl monoether and 6,O-alkyl monoether of C9-C18 or C4-C8.

Typically, when the saccharide derivative is a hexitan, the positional isomers are at least two of 2,O-alkyl monoether, 3,O-alkyl monoether—5,O-alkyl monoether and 6,O-alkyl monoether of C9-C18 or C4-C8.

Advantageously, the C4-C8 alkyl group is a C5 alkyl and the C9-C18 alkyl group is a C12 alkyl. Preferably, the saccharide derivative is selected from monoanhydrosorbitol or alkyl glucoside, and even more preferably the saccharide derivative is methyl glucoside.

The invention also relates to a mixture of C4-C8 alkyl monoether of saccharide derivative and of C9-C18 alkyl monoether of saccharide derivative, notably obtainable by the process of the invention, in which the C4-C8 alkyl monoether of saccharide derivative is a C5 alkyl monoether of saccharide derivative and the C9-C18 alkyl monoether of saccharide derivative is a C12 alkyl monoether of saccharide derivative, preferably in which said saccharide derivative is a glycosylated and/or hydrogenated and/or dehydrated saccharide, and more preferably said saccharide derivative is selected from monoanhydrosorbitol or alkyl glucoside, notably methyl glucoside.

In general, the ratio of C5 alkyl monoether of saccharide/C12 alkyl monoether of saccharide in the mixture of the invention is between 5:95 and 95:5, preferably between 20:80 and 70:30, 30:70 and 60:40, 35:65 and 55:45, 40:60 and 52:48, 42:58 and 50:50.

Use of Alkyl Monoether of Saccharide as a Surfactant and Method of Obtaining a Surfactant of this Kind The invention also relates to the use of the mixture obtained by carrying out the process according to the invention or using a mixture of C4-C8 alkyl monoether of saccharide or of saccharide derivative and C9-C18 alkyl monoether of saccharide or of saccharide derivative as a surfactant, said saccharide derivative being a glycosylated and/or hydrogenated and/or dehydrated saccharide. Preferably, said saccharide derivative is selected from monoanhydrosorbitol or alkyl glucoside, notably methyl glucoside.

The term "surfactant" or "surface-active agent" denotes a compound that reduces surface tension when it is dissolved in water or in an aqueous medium, or that reduces the interfacial tension between two liquids, between a liquid and a solid or between a liquid and a gas. As a general rule, the surface-active properties of a compound may be measured by the plate method using a platinum rod as probe (Du Nouy-Padday method, as described in J F Padday, A R Pitt, R M Pashley, *J. Chem. Soc. Faraday. Trans* 1, 1975, 71, 1919-1931). The Du Nouy-Padday method is used for measuring the equilibrium of surface tension or of dynamic surface tension at the air/liquid interface.

According to one embodiment, the mixture obtained by carrying out the process according to the invention or the mixture of C4-C8 alkyl monoether of saccharide and C9-C18 alkyl monoether of saccharide may be used in a composition containing at least two surfactants or as the only surfactant.

In one embodiment, the mixture obtained by the process of the invention or the mixture of C4-C8 alkyl monoether of saccharide and of C9-C18 alkyl monoether of saccharide may be used as a detergent, emulsifier, emulsion stabilizer, foaming agent, foam stabilizer, liposome stabilizer, dispersant and/or wetting agent. Such agents are usually employed in various domestic and industrial applications, for example as detergents for washing linen, dish-washing detergents, industrial detergents, emulsifiers in cosmetics, emulsifiers and/or stabilizers in inks, in paints and in coating compositions, and as foaming agents and/or foam stabilizers in shampoo.

Typically, the mixture of C4-C8 alkyl monoether of saccharide or of saccharide derivative and of C9-C18 alkyl monoether of saccharide or of saccharide derivative is a mixture of C5 alkyl monoether of saccharide or of saccharide derivative and of C12 alkyl monoether of saccharide or of saccharide derivative, said saccharide derivative being a glycosylated and/or hydrogenated and/or dehydrated saccharide, and preferably said saccharide derivative is a monoanhydrosorbitol or an alkyl glucoside, notably a methyl glucoside.

The invention also relates to a method for obtaining a surfactant or a surfactant composition comprising a) a first step of acetalization or trans-acetalization of a saccharide, of a saccharide derivative or of mixtures thereof with a C4-C8 aliphatic aldehyde or the acetal thereof, said saccharide derivative being a glycosylated and/or hydrogenated and/or dehydrated saccharide, b) a second consecutive or simultaneous step of acetalization or trans-acetalization of the product obtained in a), of the saccharide, saccharide derivative or mixtures thereof with a C9-C18 aliphatic aldehyde or the acetal thereof, c) a step of catalytic hydrogenolysis of the saccharide acetals obtained in b), and d) a step of recovery of the surfactant or surfactant composition obtained.

Typically, said surfactant composition is a detergent, an emulsifier, an emulsion stabilizer, a foaming agent, a foam stabilizer, a liposome stabilizer, a dispersant and/or a wetting agent.

Although having separate meanings, the terms "comprising", "containing", "having" and "consisting of" have been used interchangeably in the description of the invention, and can be replaced with one another.

The invention will be better understood on reading the following figures and examples, given purely as examples.

EXAMPLES

Example 1: Materials and Methods

Figure 1:
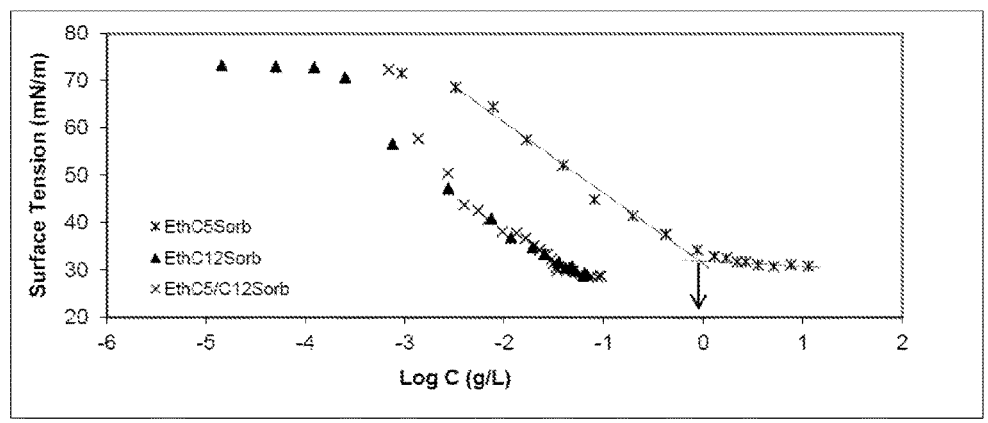
FIG. 1 shows the surface tension (mN/m) of the sorbitan ether derivatives as a function of the concentration (g/L). The critical micelle concentration (CMC) is indicated by small arrows, C5EthSorb is represented by black diamonds, C12EthSorb by black dots and the C5/C12EthSorb mixture by empty triangles.

General Procedure for Measurements of Surface Tension

Surface tension was measured at (25.0±0.1)° C. with a Krüss K100MK2 tensiometer using a platinum rod as probe. A total of 1.0 ml of water was added to the measuring vessel. When the surface tension is stable (standard deviation of the last five measurements of 0.2 mN/m), manual dilution is carried out with a concentrated solution of surfactant to its limit of solubility while maintaining constant volume.

Analytical Methods

All the reactants and solvents used for the synthesis are commercial products (supplied by SIGMA-ALDRICH and ACROS ORGANICS), which were used without further purification. All the new compounds obtained were characterized by spectroscopic data. The reactions were monitored by thin-layer chromatography using silica gel on aluminum plates (60F254). The nuclear magnetic resonance (NMR) measurements were recorded on a Bruker DRX 300 or 400 or Bruker ALS 300 spectrometer. The chemical shifts are given by reference to the central peaks of $d_6$-DMSO or $CDCl_3$ (39.5 and 77.0 ppm respectively) for $^{13}C$ NMR, and (2.50 and 7.26 ppm respectively) for $^1H$ NMR. The coupling constants J are given in hertz (Hz). The abbreviations are to be understood as follows: s=singlet, d=doublet, dd=doublet of doublets, t=triplet, q=quadruplet, m=multiplet. The separations by flash chromatography were carried out using Grace Davisil® LC60A silica gel (40-63μ). The analyses by high-performance liquid chromatography were carried out on a column using a C18 column (SPHERISORB C18, 5 μm, 250 mm×20 mm) using MeCN-water (20/80) eluent and detection by refractive index (RI).

The mass spectra were acquired in positive ion mode using a spectrometer (MicroTOFQ-II, BrukerDaltonics, Bremen) with electrospray ionization (ESI). The flow of atomizing gas is at 0.6 bar and the capillary voltage is 4.5 kV. The solutions were injected at 180 μL/h in a mixture of solvents (methanol/dichloromethane/water 45/40/15). The mass range of the analysis is 50-1000 m/z and calibration was performed with sodium formate.

All the acetals were dried over magnesium sulfate ($MgSO_4$), and filtered before hydrogenolysis.

Example 2: Synthesis of the Sorbitan Acetals

Firstly, the sugar acetals were prepared by acetalization or trans-acetalization of sugars following the procedure described in patent application FR 3 007 031. The ratio of 2:1 between the sugar and the aldehyde was not changed but 0.5 equivalent of a long-chain alkyl aldehyde or of its acetal was replaced with 0.5 equivalent of a short-chain alkyl aldehyde or of its acetal to aid dissolution of the reactants (scheme 1). The desired products were obtained in the form of a mixture of short-chain and long-chain acetals with improved yields for long-chain alkyl acetals, relative to the conventional procedure.

Scheme1. Synthesis of a mixture of sorbitan acetals

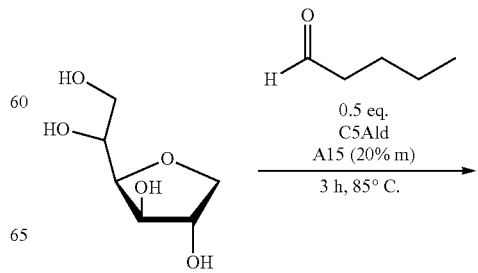

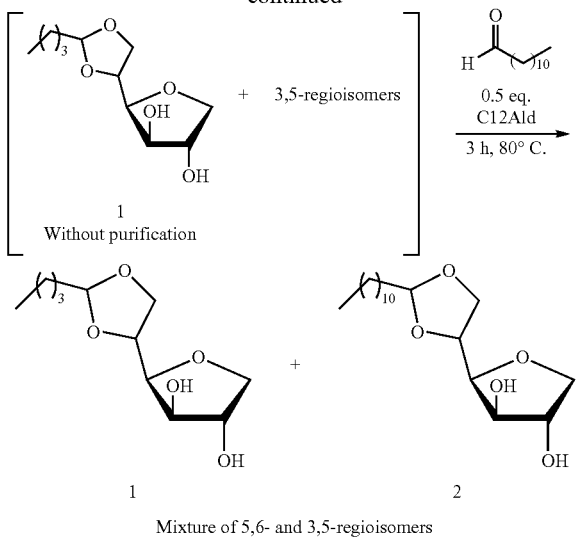

Mixture of 5,6- and 3,5-regioisomers

In order to synthesize the acetal of sorbitan dodecylidene with a better yield, sorbitan was reacted with valeric aldehyde (0.5 equivalent) in the presence of 20 wt % of AMBERLYST® 15 (A15) as acid catalyst. The reaction may be carried out using anhydrous tetrahydrofuran (1 M) or cyclopentyl methyl ether (1 M) as solvent or in conditions without solvent. Moreover, sodium sulfate (1.5 equivalent) was also added as a dehydrating agent in order to trap the water formed during the acetalization reaction, which led to an increase in sorbitan conversion. Sodium sulfate may advantageously be replaced with molecular sieves or by azeotropic removal of water. It should be noted that sodium sulfate was not added to the reaction carried out in conditions without solvent, because of the difficulties of stirring. The reaction mixture was heated at 80° C. for 3 hours, then 0.5 equivalent of dodecanal was added and the reaction mixture was stirred at 80° C. for a further 3 hours.

The results are presented in Table 1 and are compared with those obtained with dodecanal alone.

bitan (2) was obtained with an isolated yield of 39% (entry 1) in the presence of solvent and without surface-active acetal intermediate. However, with the synthesis of the mixture of 3,5- and 5,6-pentylidene-1,4-sorbitan (1) as a surfactant, the desired long-chain alkyl sorbitan acetal (2) was isolated at 81% in THF (entry 2) and at 58% in CPME (entry 3). Moreover, the isolated yield of pentylidene and dodecylidene acetal obtained was 69% of the isolated yield in THF and 62% in CPME. Without solvent, the effect is even greater. In this case, sodium sulfate was not added, with the aim of making magnetic stirring possible. In fact, the isolated yield of sorbitan dodecylidene acetal went from 36% to 82% owing to the surface-active characteristics of pentylidene sorbitan (entries 4-5). More precisely, using pentylidenesorbitan acetal (1) in situ, the degree of conversion of dodecanal went from 60% to 94% and a shorter reaction time is required. These results show that the acetal of sorbitan pentylidene allows dissolution of the long hydrophobic alkyl chains in the medium and display "solvosurfactant" properties. The use of intermediate surfactants contributes to better dissolution of the reactants by lowering the surface tension between the polar and nonpolar phases. The desired APG is thus obtained. In fact, butanol serves both as solvent and reactant, to form O-butyl glucoside, which will then be miscible with FOH during the subsequent transglycosidation. Moreover, this method could be carried out on oligosaccharides in one and the same medium, in other words in a single reactor.

Example 3 Hydrogenolysis of the C5/C12 Acetals

Hydrogenolysis of the mixture of sorbitan acetals of 3,5- and 5,6-pentylidene (1) and of dodecylidene (2) was carried

TABLE 1

Acetalization of sorbitan with a mixture of short-chain and long-chain aldehydes:

| Entry | Aldehyde | Na$_2$SO$_4$ (eq.) | Solvent | Conversion C5Ald[b] (%) | Conversion C12Ald[c] (%) | Isolated yield (1 + 2) | Ratio C5:C12[c] | Yield 2 |
|---|---|---|---|---|---|---|---|---|
| 1 | C12 | 1.5 | THF | nd | 87 | — | — | 39[d] |
| 2 | C5/12 | 1.5 | THF | 94 | 86 | 69 | 31:69 | 81[e] |
| 3 | C5/12 | 1.5 | CPME | 76 | 76 | 62 | 46:54 | 58[e] |
| 4 | C12 | 0 | without | nd | 60 (15 h) | — | — | 36[d] |
| 5 | C5/C12 | 0 | without | 96 | 94 (3 h) | 77 | 38:62 | 82[e] |

[a]Experimental conditions: Sorbitan (20 g, 122 mmol), valeric aldehyde (3.2 mL, 31 mmol), AMBERLYST ® A15 (0.5 g, 20 wt %), 80° C., 3 h, then dodecanal (6.9 mL, 31 mmol), 80° C., 3 h.
[b]The conversions were determined from the $^1$H-NMR spectra.
[c]The degrees of conversion were determined by HPLC.
[d]Isolated yield.
[e]Yield calculated from the total mass recovered and the C5/12 ratio as obtained by HPLC.

After reaction, the crude mixture was purified by silica gel column chromatography to obtain a mixture of C5/C12 acetals. The ratio of the C5 and C12 sorbitan acetals was then determined by HPLC. The weight and the yield of sorbitan dodecylidene acetal (2) were calculated from these data. The mixture of 3,5- and 5,6-O-dodecylidene-1,4-sorout using the conditions already described by the inventors in a previous French patent application No. 14/01346. The optimized hydrogenolysis conditions [5 mol % of Pd/C (5%), 120° C., 30 bar of H$_2$, CPME (0.1 M), with a mechanical stirring speed of 800 rev/min] were used for the synthesis of sorbitan monoethers in position 3, 5 and 6 obtained from sugar acetals (scheme 2).

Scheme 2. Synthesis of mixtures of sugar ethers

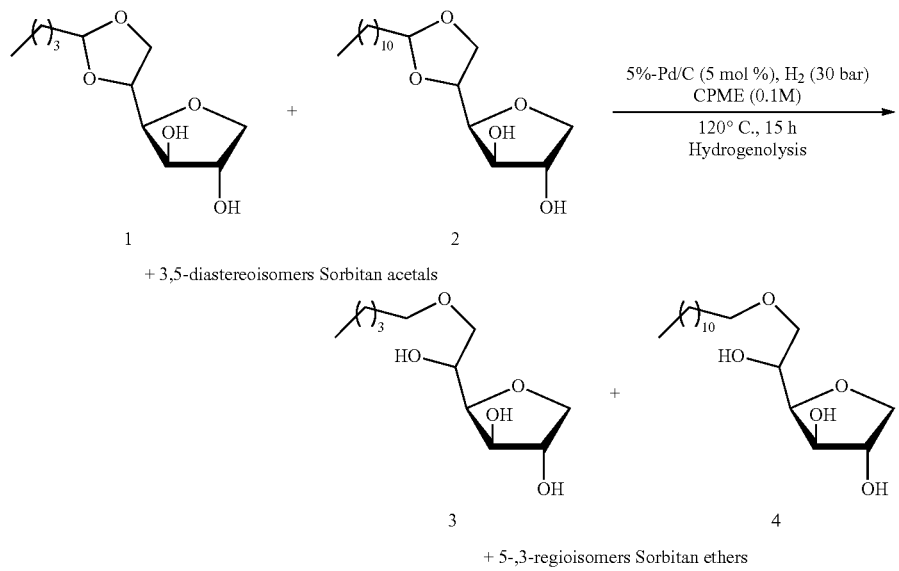

+ 3,5-diastereoisomers Sorbitan acetals

+ 5-,3-regioisomers Sorbitan ethers

TABLE 2

Hydrogenolysis of sorbitan acetals[a]:

+3,5-diastereoisomers

+5,3-regiosomers

| Entry | Sugar acetal | Conversion (1 + 2)[b](%) | Isolated yield (3 + 4)[d] | Ratio C5:C12[c] | Yield 4 | Selectivity (%) |
|---|---|---|---|---|---|---|
| 1 | C12 | 97 | — | — | 55[d] | 57 |
| 2* | C5/12 | 65 | 18 | 36:64 | 17[e] | 26 |
| 3 | C5/C12 | >98 | 89 | 48:52 | 68[e] | 69 |

[a]Experimental conditions: sorbitan (20 mmol), Pd/C (5 mol %, 5% Pd), 120° C., 30 bar H$_2$, stirring speed = 800 rpm
*magnetic stirring, 15 h.
[b]Conversions determined from the $^1$H NMR spectra.
[d]Isolated yield.
[e]Yields calculated with the C5/12 ratio.

The results are summarized in Table 2. Starting from (3,5+5,6)-dodecylidene sorbitan (entry 1), the acetal (2) was transformed completely. However, in these cases, the isolated yield of (6+5+3−)-dodecyl sorbitan (4) was only 55%. However, starting from the previous mixture of C5/C12 acetals of sorbitan (entry 2), the conversion is lower (65%). In fact, with mechanical stirring, conversion is total and the selectivity reaches 69% instead of 57% without pentylidene sorbitan acetal, to obtain the desired product with 68% yield.

Based on these results, the inventors have shown that the limiting step of acetalization with the long-chain alkyl aldehyde could be improved by using a short-chain alkyl acetal of sorbitan as an intermediate, which performs the role of "solvo-surfactant" by dispersion of the hydrophobic reactant in a polar medium. Moreover, this study showed that the long-chain alkyl sorbitan ethers can be synthesized with a better yield starting from the C5/C12 mixture.

Example 4: Physicochemical Properties of the Surfactants Synthesized

Surface-Active Properties

Several approaches may be used for studying the properties of surfactants. Firstly, surface tension tests were carried out between air and water with a view to determining the variation of the properties as a function of the length of the alkyl chain and of the polar head.

In the present study, the general characteristics of the surfactants were evaluated by measuring the reduction in saturated surface tension ($\gamma_{sat}$) and the critical micelle concentration (CMC) of the mixture (3+4) previously obtained in water at 25° C. The surface-active properties were compared against those of the pure compounds.

The Surface Tension of the Aqueous Solutions

The surface tension of aqueous solutions containing increasing concentrations of each of the compounds was measured by the Du Noüy-Padday method using a platinum rod as probe (method described in J. F. Padday, A. R. Pitt, R. M. Pashley, *J. Chem. Soc. Faraday. Trans* 1, 1975, 71, 1919-1931). The data are presented graphically in FIG. 1, showing analysis of the surface tension as a function of the concentration of the sorbitan ether derivatives (CSEthSorb (black diamonds), C12EthSorb (black lozenges), C5/C12EthSorb (black triangles)). The value of the critical micelle concentration (CMC) is shown with a small arrow for C5EthSorb.

For all the compounds, lowering of the surface tension of water is observed and the saturation value is reached at very low concentrations. According to the curves, the critical micelle concentrations (CMC) and the saturation surface tension are presented in Table 3.

TABLE 3

Minimum hydrotrope concentration (MHC) or critical micelle concentration (CMC) and surface tension of water ($\gamma_{sat}$).

| Product | Ratio (3c:3b:3a)/ (4c:4b:4a)[a] | CMC (mg/L) | $\gamma_{sat}$ (mN/m) |
|---|---|---|---|
| 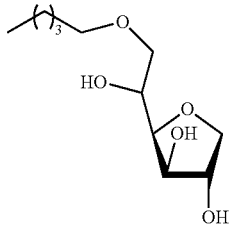<br>3c + 3b + 3a<br>5-,3-,6-regioisomers<br>C5EthSorb | 26:33:41 | 1779 | 32 |
| C12EthSorb | 27:33:40 | 30.2 | 31 |
| C5/C12EthSorb (48/52) | 37:16:47/52:38:10 | 29.8 | 30 |

[a] Ratio of measurements obtained by HPLC

We may conclude from these results that for all the compounds, lowering of the surface tension of water is observed and the saturation value is reached at very low concentrations. Moreover, it may be noted that the C5/C12 mixture, in the ratio 48:52, gave surface-active properties similar to those of pure sorbitan dodecyl ether (by CMC for C5/C12 of 29.8 mg/L and 30.2 mg/L for C12). These results demonstrate the synergy of the C5/C12 mixture. Thus, pentyl sorbitan (3) makes it possible to increase the solubility of the mixture while obtaining surface-active characteristics similar to those of the pure dodecyl sorbitan (4). In fact, the dodecyl sorbitans cause a decrease in surface tension of water even at low concentration of the mixture of surfactants. With sorbitan pentyl ether, a concentration of 1179 mg/L is necessary to lower the surface tension by 31 mN/m whereas a concentration of 29.8 mg/L of the C5/C12 mixture with only 48% of pentyl sorbitan is sufficient to reach this same surface tension.

Example 5: Synthesis of C5/C12 Acetals of Methyl Glucopyranoside 4,6-O-Dodecylidene-α-D-methyl glucopyranoside was synthesized as in example 2 with valeric aldehyde (0.5 equivalent) in the presence of 20 wt % of AMBERLYST® 15 (A15) as acid catalyst (see scheme 3). As mentioned above, the reaction may be carried out using anhydrous tetrahydrofuran (1 M) or cyclopentyl methyl ether (1 M) as solvent or in conditions without solvent. Moreover, sodium sulfate (1.5 equivalent) was also added as dehydrating agent. The reaction mixture was heated at 80° C. for 3 hours, then dodecanal (0.5 equivalent) was added and the reaction mixture was stirred at 80° C. for a further 3 hours.

Scheme 3. Synthesis of C5/C12 acetals of methyl glucopyranoside

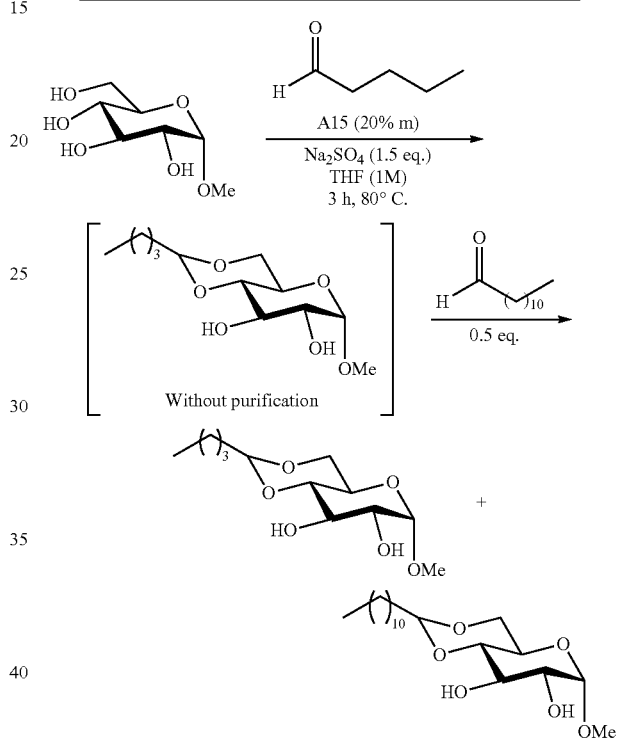

The results are presented in Table 4 and are compared with those obtained with dodecanal alone.

TABLE 4

Acetalization of methyl glucoside using a mixture of short-chain and long-chain aldehydes

| Entry | Na$_2$SO$_4$ (eq.) | Aldehyde | Conversion C5Ald[a] | Conversion C12Ald[b] | Isolated yield | Ratio C5:C12[b] | Yield C12 |
|---|---|---|---|---|---|---|---|
| 1 | 1.5 | C12 | — | 76 | — | — | 28 |
| 2 | 0.75 + 0.75 | C5/C12 | 64 | 72 | 41 | 45:55 | 39 |

[a] Conversions determined by $^1$H NMR.
[b] Ratios determined by HPLC.

After reaction, the crude mixture was purified by silica gel column chromatography to give a mixture of C5/C12 acetals of methyl glucoside. The ratio of the C5 and C12 acetals of methyl glucoside was then determined by HPLC. The weight and the yield of acetal dodecylidene of methyl glucoside were calculated from these data.

Without an intermediate surfactant, 4,6-O-decanylidene-α-D-methyl glucopyranoside was obtained with an isolated yield of 28% (entry 1). However, during synthesis of the 4,6-O-pentylidene-α-D-methyl glucopyranoside, the desired long-chain alkyl acetal of methyl α-D-glucopyranoside was isolated in THF with an improved yield of about 39% (entry 2). These results demonstrate that 4,6-O-pentylidene α-D-methyl glucopyranoside allows dissolution of the hydrophobic long-chain alkyl.

Example 6: Hydrogenolysis of the C5/C12 Ethers of Methyl Glucopyranoside

Hydrogenolysis of the 4,6-O-dodecylidene-α-D-methyl glucopyranoside mixture was carried out using the conditions already described in example 3 (see scheme 4).

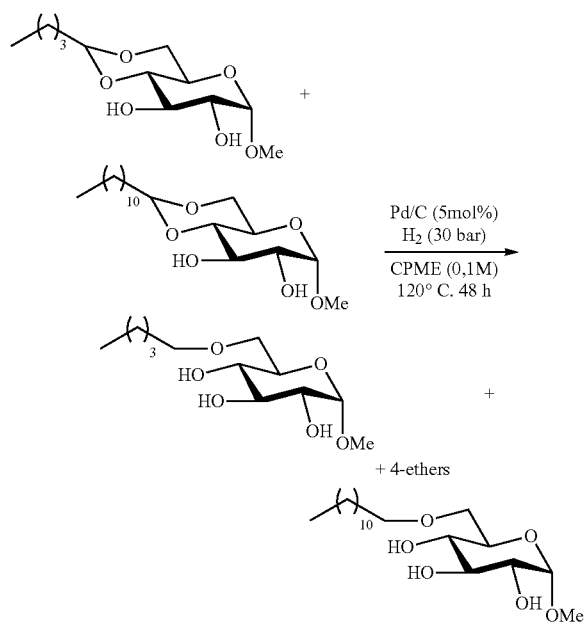

Scheme 4. Synthesis of the C5/C12 EthMeGlu

TABLE 5

Hydrogenolysis of the acetals of methyl glucoside[a]:

| Entry | Ratio of Acetals C5:C12[b] | Conv.[c] | Isolated yield C5/C12[d] | Ratio of Ethers C5:C12[b] | Calculated yield C12[e] |
|---|---|---|---|---|---|
| 1 | — | 59 | — | — | 51 |
| 2 | 45:55 | 68 | 28 | 46:54 | 28 |

[a]Experimental conditions: acetals of methyl glucoside (20 mmol), of Pd/C (5 mol %, 5% of Pd), CPME (200 mL), 120° C., 30 bar of H₂, the stirring speed is 800 revolutions per minute, 15 h.
[b]Ratio determined by HPLC.
[c]Conversions determined from the ¹H NMR spectra.
[d]Isolated yield.
[e]Yield calculated with the C5/12 ratio.

The results are summarized in Table 5. Starting from (4,6)-O-dodecylidene-α-D-methyl glucopyranoside (entry 1), the sugar acetal was converted at 59%. However, in these cases, the calculated yield of (6+4)-O-dodecyl-α-D-methyl glucopyranoside was only 51%. However, starting from the previous mixture of C5/C12 acetals of methyl glucoside (entry 2), the conversion is higher (68%). In fact, dodecyl-α-D-methyl glucopyranoside was obtained with only 28% of calculated yield. Use of the glucoside acetal with a short alkyl chain does not allow the yield of long-chain alkyl glucoside ether to be increased.

Example 7: Physicochemical Properties of the Surfactants Synthesized

Surface-Active Properties

The general characteristics of the surfactants were evaluated as in example 4 by measuring the reduction in saturated surface tension ($\gamma_{sat}$) and the critical micelle concentration (CMC) of the mixture (C5/C12 MeGlu) obtained previously in water at 25° C. The surface-active properties were compared with pure compounds.

The Surface Tension of the Aqueous Solutions

Figure 2:
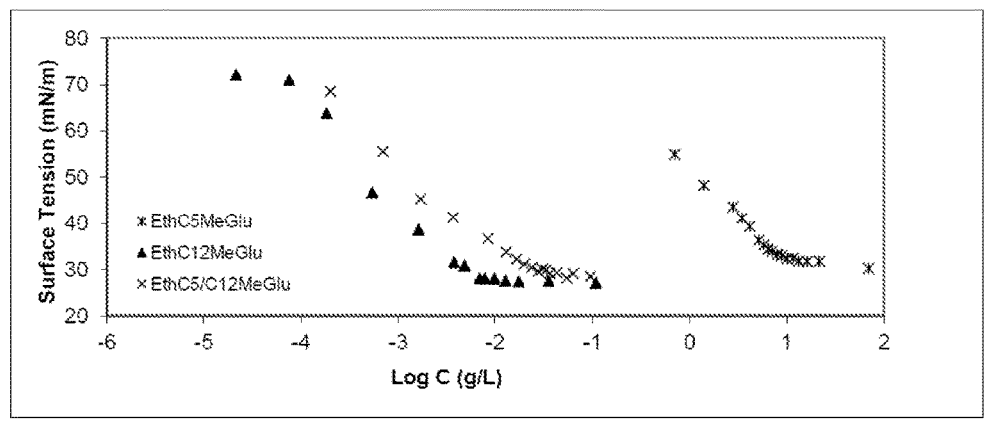
FIG. 2 shows the surface tension (mN/m) of the ether derivatives of methyl glucoside as a function of the concentration (g/L). C5EthMeGlu is represented by black stars, C12EthMeGlu by black diamonds, and the C5/C12EthMeGlu mixture by black crosses.

The surface tension of aqueous solutions containing increasing concentrations of each of the compounds was measured by the plate method using a platinum rod as probe (Du Nouy-Padday method as described in J F Padday, A R Pitt, R M Pashley, *J. Chem. Soc. Faraday. Trans* 1, 1975, 71, 1919-1931). The data are shown in FIG. 2, showing analysis of the surface tension from the concentration of the ether derivatives of methyl glucoside (C5EthMeGlu (black star), C12EthMeGlu (black diamond), C5/C12EthMeGlu (black cross)).

For all the compounds, lowering of the surface tension of water is observed and the saturation value is reached at very low concentrations. According to the curves, the critical micelle concentrations (CMC) and the saturation surface tension are given in Table 6.

TABLE 6

Minimum hydrotrope concentration (MHC) or critical micelle concentration (CMC) and surface tension of water ($\gamma_{sat}$)

| Product | CMC (mg/L) | $\gamma_{sat}$ (mN/m) |
|---|---|---|
| C5EthMeGlu | 8199 | 32 |
| C12EthMeGlu | 4.5 | 28 |
| C5/C12EthMeGlu (46/54) | 18.9 | 30 |

Based on these results and as mentioned above for the sorbitan ethers, we may conclude that for all the compounds, a lowering of the surface tension of water is observed and the saturation value is reached at very low concentrations. Moreover, similar surface-active properties are also observed between the C5/C12 mixture, in the ratio 46:54 and the pure dodecyl of α-D-methyl glucopyranoside (with a CMC of 18.9 mg/L for the C5/C12 mixture and of 4.5 mg/L for C12). As observed previously in example 4 for the sorbitan ethers, these results confirm the synergy of the C5/C12 mixture. In fact, pentyl α-D-methyl glucopyranoside performs the role of "solvo-surfactant" by improving the solubility of the mixture, and more particularly of dodecyl α-D-methyl glucopyranoside. Moreover, at low concentration, dodecyl α-D-methyl glucopyranoside lowers the surface tension of water. With pentyl α-D-methyl glucopyranoside, a concentration of 8199 mg/L is necessary to lower the surface tension by 32 mN/m whereas only 18.9 mg/L of the C5/C12 mixture is necessary to reach a surface tension of 30 mN/m.

The invention claimed is:
1. A process for obtaining a mixture of C4-C8 alkyl monoether of saccharide and/or of saccharide derivative and of C9-C18 alkyl monoether of saccharide and/or of saccharide derivative, said saccharide derivative being a glycosylated and/or hydrogenated and/or dehydrated saccharide, said process comprising:
   a) a first step of acetalization or trans-acetalization of a saccharide, of saccharide derivative or of mixtures thereof with a C4-C8 aliphatic aldehyde or the acetal thereof,
   b) a second consecutive or simultaneous step of acetalization or trans-acetalization of the product obtained in a), of the saccharide, of the saccharide derivative or of mixtures thereof, with a C9 to C 18 aliphatic aldehyde or the acetal thereof,
   c) a step of catalytic hydrogenolysis of the acetals of saccharide and/or saccharide derivative obtained in b), and
   d) a step of recovery of a mixture of C4-C8 alkyl monoether of saccharide and/or of saccharide derivative and of C9-C18 alkyl monoether of saccharide and/or of saccharide derivative.

2. The process as claimed in claim 1, in which said saccharide derivative is a monoanhydrosaccharide or a C1-C4 alkyl glycoside.

3. The process as claimed in claim 1, in which said saccharide derivative is an anhydrosaccharide or an alkyl glycoside.

4. The process as claimed claim 1, in which said saccharide is a monosaccharide, a disaccharide or a trisaccharide.

5. The process as claimed claim 1, in which said saccharide and/or derivative of saccharide comprises from 4 to 7 carbon atoms.

6. The process as claimed in claim 1, in which said saccharide derivative is a sugar alcohol selected from the group consisting of erythritol, threitol, arabitol, xylitol, ribitol, mannitol, sorbitol, galactitol, iditol, volemitol, isomalt, maltitol, lactitol, maltotriitol, maltotetraitol, polyglycitol and the process further comprises a dehydration step, before said step a) of first acetalization or trans-acetalization.

7. The process as claimed in claim 1, in which said saccharide derivative is an alkyl glycoside selected from a group consisting of methyl glucoside, ethyl glucoside, propyl glucoside, butyl glucoside, methyl xyloside, ethyl xyloside, propyl xyloside, butyl xyloside, methyl mannoside, ethyl mannoside, propyl mannoside, butyl mannoside, methyl galactoside, ethyl galactoside, propyl galactoside and butyl galactoside.

8. The process as claimed in claim 1, in which the C4-C8 aliphatic aldehyde is a C5 aliphatic aldehyde or the acetal of the latter and/or the C9 to C18 aliphatic aldehyde or the acetal of the latter is a C12 aliphatic aldehyde or the acetal thereof.

9. The process as claimed claim 1, in which the molar ratio (C4-C8 or C9-C18 aliphatic aldehyde or acetal thereof):(saccharide, the derivative of saccharide or mixtures thereof) is between 5:1 and 1:5.

10. The process as claimed in claim 1, in which the first and/or second step of acetalization or trans-acetalization is carried out in the presence of an acid catalyst, wherein the first and/or second step of acetalization or transacetalization is carried out in conditions without solvent or in the presence of a polar solvent.

11. The process as claimed claim 1, in which hydrogenolysis is carried out at a temperature between 80 and 140° C. and/or at a pressure between 15 and 50 bar, in the presence of a catalyst based on precious metals, on base metals in the group of ferrous metals.

12. A composition comprising a mixture of positional isomers of C4-C8 alkyl monoether of saccharide or of saccharide derivative and of positional isomers of C9-C18 alkyl monoether of saccharide or of saccharide derivative, in which the saccharide derivative is a glycosylated and/or hydrogenated and/or dehydrated saccharide, and the saccharide is a hexose.

13. The composition as claimed in claim 12, in which the C4-C8 alkyl group is a C5 alkyl and the C9-C18 alkyl group is a C12 alkyl, the saccharide derivative being selected from monoanhydrosorbitol or alkylglucoside.

14. The composition as claimed claim 12, in which the ratio of C5 alkyl monoether of saccharide or of saccharide derivative/C 12 alkyl monoether of saccharide or of saccharide derivative is between 5:95 and 95:5.

15. The process as claimed in claim 5, wherein said saccharide and/or saccharide derivative is selected from:
   a hexose selected from a group consisting of glucose, mannose, galactose, allose, altrose, gulose, idose or talose, and
   a hexitan selected from a group consisting of 1,4-anhydro-D-sorbitol; 1,5-anhydro-D-sorbitol; 3,6-anhydro-D-sorbitol; 1,4 (3,6)-anhydro-D-mannitol; 1,5-anhydro-D-mannitol; 3,6-anhydro-D-galactitol; 1,5-anhydro-D-galactitol; 1,5-anhydro-D-talitol; and 2,5-anhydro-L-iditol.

16. The composition as claimed in claim 12, wherein the saccharide derivative is methyl glucoside.

17. A method for reducing the surface tension of a liquid, said method comprising:
   contacting a liquid with:
      a composition comprising a mixture of C4-C8 alkyl monoether of saccharide and/or of saccharide derivative and of C9-C18 alkyl monoether of saccharide and/or of saccharide derivative, or
      a composition comprising a mixture of positional isomers of C4-C8 alkyl monoether of saccharide or of saccharide derivative and of positional isomers of C9-C18 alkyl monoether of saccharide or of saccharide derivative, in which the saccharide derivative is a glycosylated and/or hydrogenated and/or dehydrated saccharide, and the saccharide is a hexose, or
      a mixture of C4-C8 alkyl monoether of saccharide and/or of saccharide derivative and of C9-C18 alkyl monoether of saccharide and/or of saccharide derivative, said saccharide derivative being a glycosylated and/or hydrogenated and/or dehydrated saccharide, obtained by a process comprising:
         a) a first step of acetalization or trans-acetalization of a saccharide, of saccharide derivative or of mixtures thereof with a C4-C8 aliphatic aldehyde or the acetal thereof,
         b) a second consecutive or simultaneous step of acetalization or trans-acetalization of the product obtained in a), of the saccharide, of the saccharide derivative or of mixtures thereof, with a C9 to C 18 aliphatic aldehyde or the acetal thereof,
         c) a step of catalytic hydrogenolysis of the acetals of saccharide and/or of saccharide derivative obtained in b), and
         d) a step of recovery of the mixture of C4-C8 alkyl monoether of saccharide and/or of saccharide derivative and of C9-C18 alkyl monoether of saccharide and/or of saccharide derivative.

18. The method as claimed in claim 17, wherein the mixture of C4-C8 alkyl monoether of saccharide and/or of saccharide derivative and of C9-C18 alkyl monoether of saccharide and/or of saccharide derivative is a mixture of C5 alkyl monoether of saccharide and/or of saccharide derivative and of C12 alkyl monoether of saccharide and/or of saccharide derivative and in which said saccharide derivative is selected from monoanhydrosorbitol or alkyl glucoside.

19. The method as claimed in claim 17, wherein said saccharide derivative is methyl glucoside.

20. The composition as claimed in claim 12, said composition being a surfactant composition, and wherein said surfactant composition is selected from a detergent, an emulsifier, an emulsion stabilizer, a foaming agent, a foam stabilizer, a liposome stabilizer, a dispersant, and a wetting agent.

* * * * *